United States Patent [19]
Labat et al.

[11] Patent Number: 5,922,910
[45] Date of Patent: Jul. 13, 1999

[54] SYNTHESIS OF CARBOXYALKYLTHIOSUCCINIC ACIDS

[75] Inventors: Yves Labat; Jean-Pierre Muller, both of Pau, France

[73] Assignee: Elf Atochem S.A., France

[21] Appl. No.: 09/139,647

[22] Filed: Aug. 25, 1998

[30] Foreign Application Priority Data

Aug. 27, 1997 [FR] France .................................. 97 10707

[51] Int. Cl.$^6$ .................................................. C07C 35/00
[52] U.S. Cl. ............................................................ 562/594
[58] Field of Search ............................................ 562/594

[56] References Cited

U.S. PATENT DOCUMENTS 3,909,493  9/1975  Gilles ...................................... 260/45.7

FOREIGN PATENT DOCUMENTS

| 2251448 | 4/1973 | Germany . |
|---|---|---|
| 8-259732 | 10/1996 | Japan . |
| 8-277481 | 10/1996 | Japan . |
| 8-283783 | 10/1996 | Japan . |
| 8-311055 | 11/1996 | Japan . |

OTHER PUBLICATIONS

"Beilsteins Handbuch Der Organischen Chemie", vol. III, (1962) 4th Ed., Suppl. 3, p. 925 (Letter dated Jun. 22, 1998—to French Patent Office/translation attached).

"Uber Einige Dialkylsulfidtricarbonsauren" Erik Larsson, pp. 3–7, (Chalmers Univ. Technol., Sweden)—Chemical Abstract attached. 1997.

*Primary Examiner*—Samuel Barts
*Attorney, Agent, or Firm*—Bell, Boyd & Lloyd

[57] ABSTRACT

Process for the preparation of a carboxyalkylthiosuccinic acid of formula

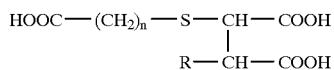

in which n=1 to 3 and R=H or $CH_3$, a mercapto ester of formula $HS-(CH_2)_n-COOR'$ in which R' is a $C_1$ to $C_4$ alkyl radical, is reacted, in aqueous medium and without a catalyst, with maleic acid, citraconic acid or their anhydride. The invention is more particularly directed towards the preparation of carboxyethylthiosuccinic acid (CETSA).

12 Claims, No Drawings

SYNTHESIS OF CARBOXYALKYLTHIOSUCCINIC ACIDS

DESCRIPTION

1. Field of the Invention

The present invention, which concerns the field of polycarboxylic acids, relates to the synthesis of carboxyalkylthiosuccinic acids and more particularly to that of carboxyethylthiosuccinic acid (referred to hereinbelow by the abbreviation CETSA).

2. Background of the Invention

This known compound of formula:

$$HOOC-CH_2CH_2-S-CH-COOH$$
$$| $$
$$CH_2-COOH$$

is especially useful as a corrosion inhibitor (patent application JP 08-277,481), as a shaping additive for polymers (patent application JP 08-259,732) or as a constituent of detergent compositions (patent application JP 08-283,783).

According to patent application JP 08-311,055, CETSA is prepared by reaction of mercaptopropionic acid with maleic anhydride, in a polar solvent such as methyl ethyl ketone and in the presence of a catalyst consisting of an ion-exchange resin. Mercaptopropionic acid is generally obtained by acid hydrolysis of alkyl mercaptopropionates and more particularly that of methyl mercaptopropionate (MMP hereinbelow).

DESCRIPTION OF THE INVENTION

It has now been found that CETSA can be obtained directly and without a catalyst by reacting MMP with maleic acid or its anhydride in aqueous medium. Surprisingly, the addition of an acid catalyst such as sulphuric acid or p-toluenesulphonic acid is not necessary for the addition reaction of the SH function of MMP on the double bond, nor, especially, for the hydrolysis of the intermediate ester into CETSA:

$$HS-CH_2CH_2-COOCH_3 + \begin{array}{c} CH-COOH \\ \| \\ CH-COOH \end{array}$$

$$\downarrow H_2O$$

$$HOOC-CH_2CH_2-S-CH-COOH + CH_3OH$$
$$|$$
$$CH_2-COOH$$

By replacing the maleic acid by citraconic acid or its anhydride, 2-carboxyethylthio-3-methylsuccinic acid can be obtained in the same way. The MMP can also be replaced by other mercapto esters such as, for example, methyl thiolglycolate, ethyl thioglycolate or ethyl mercaptopropionate.

The subject of the invention is thus a process for the preparation of carboxyalkylthiosuccinic acids of general formula:

$$HOOC-(CH_2)_n-S-CH-COOH$$
$$|$$
$$R-CH-COOH$$

in which n is an integer ranging from 1 to 3 and R denotes a hydrogen atom or a methyl radical, characterized in that it consists essentially in reacting, in an aqueous medium and in the absence of a catalyst, a mercapto ester of general formula:

$$HS-(CH_2)_n-COOR'$$

in which n has the same meaning as above and R' represents an alkyl radical containing from 1 to 4 carbon atoms, with maleic acid, citraconic acid or their anhydrides.

The reaction can be carried out at a temperature between 60 and 140° C. but is advantageously carried out between 80 and 120° C., and even more preferably at reflux. Depending on the reaction temperature chosen and on the composition of the water/alcohol mixture to be removed, the pressure can range from 1 to 4 bar; it is preferably between 1 and 2 bar, and even more preferably equal to atmospheric pressure.

The reagents (mercapto ester and maleic or citraconic acid or anhydride) are preferably used in essentially equimolar amounts, but it would not be considered a departure from the scope of the present invention to use them in a mercapto ester/maleic or citraconic acid or anhydride molar ratio ranging from 0.8 to 1.4, in particular between 1 and 1.2.

The reaction is advantageously carried non-continuously (batchwise) but it can also be carried out continuously in stirred cascade reactors. Whether the process is performed batchwise or continuously, it is essential to distil off the alcohol R'OH released. The content of reagents and/or carboxylalkyl-thiosuccinic acid in the reaction medium can vary within a wide range during the synthesis, taking into account the permanent removal of the water/alcohol mixture; a large excess of water favours the removal of the alcohol but can slow down the completion of the reaction. In order to ensure a uniform reflux and the best possible removal of the alcohol, it is advantageous to add water periodically during the synthesis. It is also recommended to maintain a mercapto ester concentration of between 2 and 5 mol/liter of solution in the reaction medium.

The carboxyalkylthiosuccinic acid can be isolated from the reaction mixture by precipitation on returning to room temperature; it can be purified by recrystallization from water.

The example which follows illustrates the invention without limiting it.

EXAMPLE 82 g (0.83 mol) of maleic anhydride and 250 g of water were introduced into a thermostatically-controlled and stirred reactor, and the mixture was then brought to reflux over 30 minutes. 100 g (0.83 mol) of MMP were then introduced and the mixture was refluxed for 2 hours. The methanol released was distilled off continuously and the reaction volume was kept constant by addition of water (620 g). After refluxing for 8 hours at 100° C., the mixture was cooled and a solid white precipitate was obtained, which, on filtration, gave 240 g of a product containing 121 g (0.545 mol) of CETSA, along with 0.5 g of MMP, 11 g of thioesters and 108 g of water. The filtrate (131 g) which contained 52 g (0.23 mol) of CETSA can be recycled in a new operation.

After drying, a crude product melting at 152° C. was obtained in a purity, measured by NMR, of 93%.

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims. The above references are hereby incorporated by reference.

We claim:

1. Process for the preparation of a carboxyalkylthiosuccinic acid of formula:

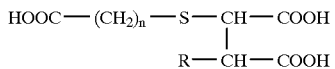

in which n is an integer ranging from 1 to 3 and R denotes a hydrogen atom or a methyl radical, consisting essentially of reacting, in an aqueous medium, a mercapto ester of formula:

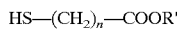

in which n has the same meaning as above and R' represents an alkyl radical containing from 1 to 4 carbon atoms, with maleic acid, citraconic acid or their anhydrides.

2. Process according to claim 1, wherein the reaction is carried out at a temperature between 80 and 140° C.

3. Process according to claim 1, wherein the process is performed at a pressure ranging from 1 to 4 bar.

4. Process according to claim 1, wherein the mercapto ester/maleic or citraconic acid or anhydride molar ratio is between 0.8 and 1.4.

5. Process according to claim 1, wherein the alcohol R'OH formed is distilled off continuously.

6. Process according to claim 1, wherein carboxyethylthiosuccinic acid is prepared from methyl mercaptopropionate and maleic acid or its anhydride.

7. Process according to claim 2, wherein the temperature is between 80 and 120° C.

8. Process according to claim 7, wherein the temperature is at reflux.

9. Process according to claim 3, wherein the pressure is between 1 and 2 bar.

10. Process according to claim 9, wherein the pressure is atmospheric.

11. Process according to claim 4, wherein the molar ratio is between 1 and 1.2.

12. Process according to claim 11, wherein the molar ratio is about 1.

* * * * *